(12) United States Patent
Schneider

(10) Patent No.: US 8,960,086 B2
(45) Date of Patent: Feb. 24, 2015

(54) SYSTEMS AND METHODS FOR VARYING THE REPEAT PITCH DISTANCE OF A SUBSTRATE FOR USE WITH ABSORBENT ARTICLES

(75) Inventor: Uwe Schneider, Cincinatti, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1159 days.

(21) Appl. No.: 12/492,388

(22) Filed: Jun. 26, 2009

(65) Prior Publication Data
US 2010/0331799 A1  Dec. 30, 2010

(51) Int. Cl.
| | |
|---|---|
| *B65H 23/00* | (2006.01) |
| *A61F 13/15* | (2006.01) |
| *B29C 55/18* | (2006.01) |
| *B41F 5/24* | (2006.01) |
| *B41F 17/00* | (2006.01) |
| *B29C 55/06* | (2006.01) |
| *B29C 55/08* | (2006.01) |

(52) U.S. Cl.
CPC ..... *A61F 13/15707* (2013.01); *A61F 13/15772* (2013.01); *B29C 55/18* (2013.01); *B41F 5/24* (2013.01); *B41F 17/007* (2013.01); *B29C 55/06* (2013.01); *B29C 55/08* (2013.01)
USPC .............................. 101/3.1; 101/248; 101/483

(58) Field of Classification Search
CPC ........... B65H 2301/50; B65H 2301/51; B65H 2301/5111; B65H 2301/512; B65H 2301/5124
USPC ........................................... 101/3.1, 248, 483
See application file for complete search history.

(56) References Cited

U.S. PATENT DOCUMENTS

| | | | |
|---|---|---|---|
| 3,518,940 A | * | 7/1970 | Charles et al. ................ 101/223 |
| 4,116,892 A | | 9/1978 | Schwartz |
| 4,285,100 A | | 8/1981 | Schwartz |
| 4,893,559 A | | 1/1990 | Sillars |
| 5,009,157 A | | 4/1991 | Rogge et al. |
| 5,010,817 A | | 4/1991 | Grosshauser |
| 5,143,679 A | | 9/1992 | Weber et al. |

(Continued)

FOREIGN PATENT DOCUMENTS

| | | |
|---|---|---|
| EP | 1884360 A2 | 2/2008 |
| GB | 2 102 733 A | 2/1983 |

(Continued)

OTHER PUBLICATIONS

International Search Report, dated Sep. 2, 2010, 7 pages.

*Primary Examiner* — David Banh
(74) *Attorney, Agent, or Firm* — Charles R. Matson; Abbey A. Lopez; Sarah M. DeCristofaro

(57) ABSTRACT

Apparatuses and methods for producing an absorbent article are provided. Graphics are printed on a substrate, where consecutive graphics are separated in the machine direction by a first repeat pitch length. The substrate is activated, or incrementally stretched, in a first direction to define a second repeat pitch distance. The second repeat pitch distance is substantially equal to the pitch length of the absorbent article pitch length. The substrate is activated, or incrementally stretched, in the machine direction subsequent to printing to increase the repeat pitch distance. The substrate may be activated in the cross direction to increase the width of the substrate. Only portions of the substrate may undergo activation. The activation may be performed with rollers and/or stamping.

10 Claims, 12 Drawing Sheets

(56) References Cited

U.S. PATENT DOCUMENTS

| | | | |
|---|---|---|---|
| 5,156,793 | A | 10/1992 | Buell et al. |
| 5,554,144 | A | 9/1996 | Roe et al. |
| 5,932,039 | A * | 8/1999 | Popp et al. .................. 156/64 |
| 6,120,632 | A | 9/2000 | Dragoo et al. |
| 6,500,377 | B1 | 12/2002 | Schneider et al. |
| 6,811,239 | B1 | 11/2004 | Salacz |
| 7,368,027 | B2 | 5/2008 | Schneider et al. |
| 7,820,003 | B2 | 10/2010 | Tachibana et al. |
| 2002/0105110 | A1 * | 8/2002 | Dobrin et al. ................ 264/154 |
| 2002/0166617 | A1 * | 11/2002 | Molander et al. ............ 156/73.1 |
| 2003/0136495 | A1 | 7/2003 | Miller et al. |
| 2003/0234069 | A1 * | 12/2003 | Coenen et al. ................ 156/64 |
| 2004/0019400 | A1 * | 1/2004 | Popp et al. ................... 700/125 |
| 2004/0044322 | A1 * | 3/2004 | Melius ....................... 604/385.01 |
| 2005/0092427 | A1 * | 5/2005 | Vergona ....................... 156/250 |
| 2006/0068168 | A1 | 3/2006 | Olson et al. |
| 2006/0082012 | A1 * | 4/2006 | Webb et al. ................ 264/172.12 |
| 2006/0288547 | A1 * | 12/2006 | Jackson ............................ 26/87 |
| 2007/0040301 | A1 * | 2/2007 | Jackson ......................... 264/290.2 |
| 2008/0023879 | A1 * | 1/2008 | Schneider ..................... 264/288.4 |
| 2008/0192105 | A1 * | 8/2008 | Sembower et al. ............ 347/124 |
| 2008/0260996 | A1 * | 10/2008 | Heilman et al. ............... 428/141 |
| 2008/0264280 | A1 * | 10/2008 | Baggot et al. .................. 101/248 |

FOREIGN PATENT DOCUMENTS

| | | |
|---|---|---|
| WO | WO 98/21137 A1 | 5/1998 |
| WO | WO 2007/024327 A1 | 3/2007 |

\* cited by examiner

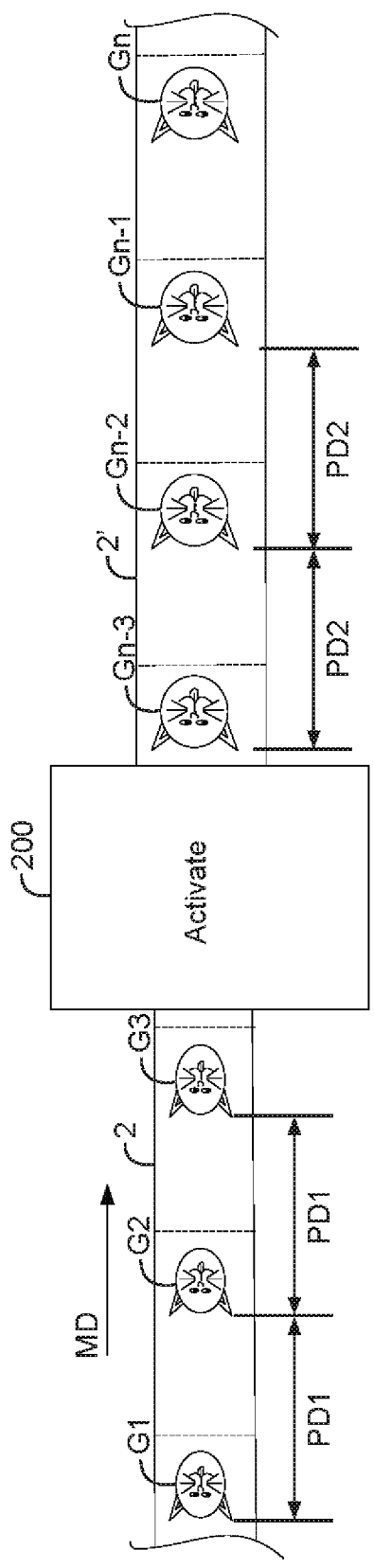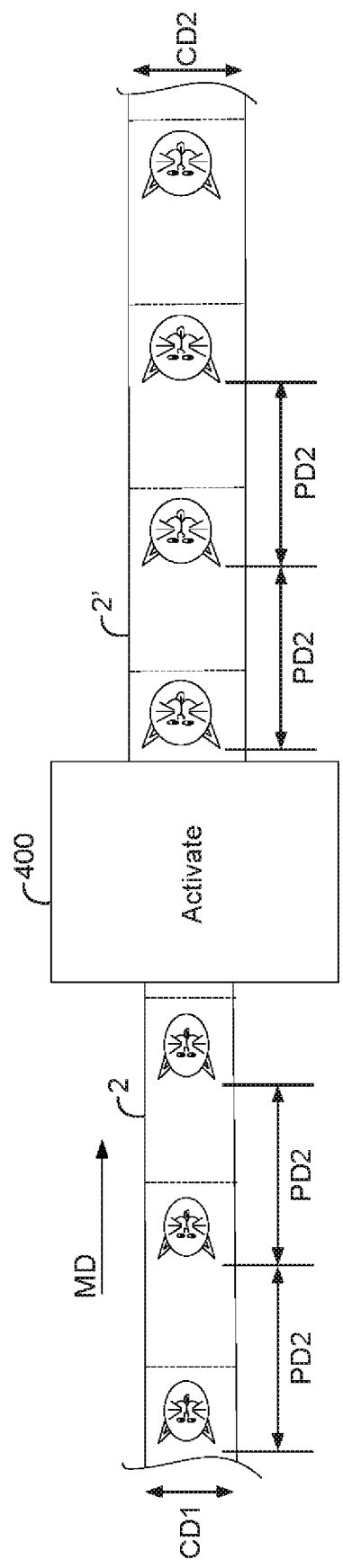

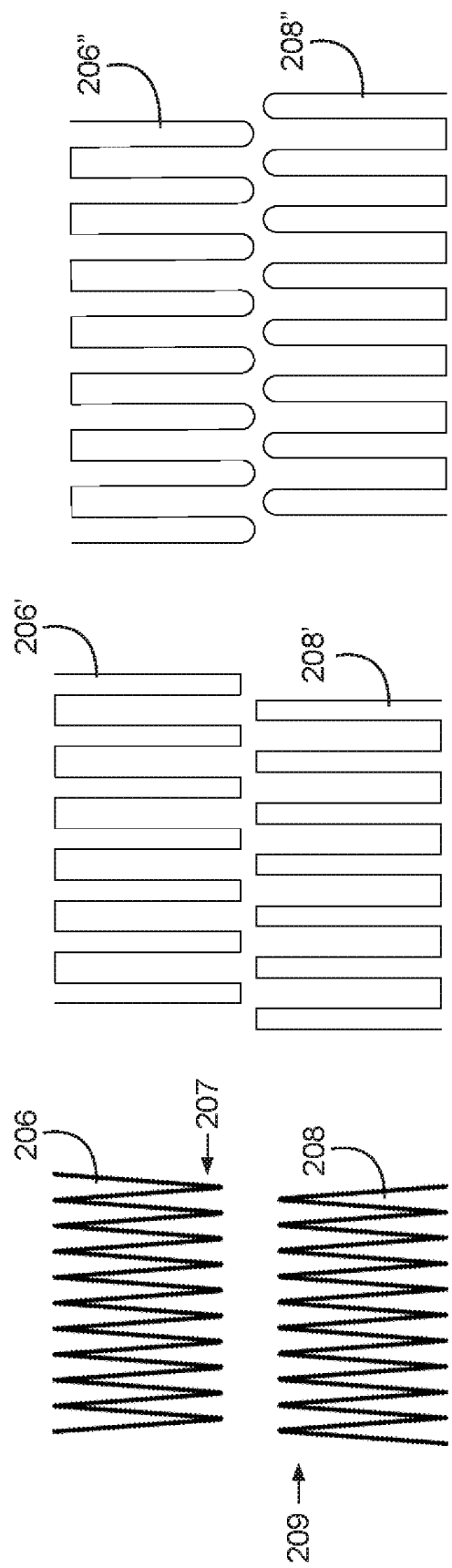

SYSTEMS AND METHODS FOR VARYING THE REPEAT PITCH DISTANCE OF A SUBSTRATE FOR USE WITH ABSORBENT ARTICLES

FIELD OF THE INVENTION

The present disclosure generally relates to printing and activating apparatuses and methods for printing a series of graphics on a substrate, and more particularly relates to apparatuses and methods for printing graphics with consecutive graphics separated in a machine direction by a first repeat pitch, activating the substrate to define a second repeat pitch separating the consecutive graphics on the substrate, and using the activated substrate in the production of absorbent articles.

BACKGROUND OF THE INVENTION

Along an assembly line, diapers and various types of other disposable absorbent articles may be assembled by adding components to and otherwise modifying an advancing, continuous web of material. Webs of material and component parts used to manufacture diapers, training and pull-up pants, incontinence briefs and undergarments, cleaning and dusting devices, and feminine hygiene garments may include: backsheets, topsheets, absorbent cores, front and/or back ears, fastener components, and various types of elastic webs and components such as leg elastics, barrier leg cuff elastics, and waist elastics, for example. In some processes, graphics are printed on an individual substrate that is ultimately used in the assembly of the absorbent articles. The graphics may be printed at a repeat pitch distance, which may be dictated, in part, by a printing plate configuration. Depending on the size of the absorbent article, the repeat pitch length of the graphics may vary. For example, an absorbent article of a first size may require a first repeat pitch length, while an absorbent article of a second larger size may require a second repeat pitch length, where the second repeat pitch length is greater than the first repeat pitch length. Accordingly, when producing absorbent articles of different sizes, it may be required to modify the printing process, such as changing the printing plates, for example, in order to print graphics at different repeat pitch lengths. Changing the printing configuration, such as the printing plates, may be both time consuming and costly. Additionally, in many cases, the production line must be stopped while the tooling reconfiguration is transpiring.

SUMMARY OF THE INVENTION

In one non-limiting embodiment, a substrate is provided for use in the production of a series of individual absorbent articles, where the individual absorbent articles each define a pitch length in a machine direction. In one non-limiting embodiment, the substrate is fed onto a rotating central impression cylinder and moved past a printing station arranged adjacent an outer surface of the central impression cylinder, where the printing station comprises a printing plate. A series of graphics can be printed on the substrate by moving the printing plate into contact with the substrate, where consecutive graphics on the substrate are separated in the machine direction by a first repeat pitch distance. In one non-limiting embodiment, the substrate is activated to provide an activated region wherein the substrate is stretched in the machine direction. Once stretched in the machine direction, a second repeat pitch distance separating consecutive graphics on the substrate is defined. In one non-limiting embodiment, the second repeat pitch distance is substantially equal to the pitch length of the individual absorbent articles.

In another non-limiting embodiment, a substrate is provided for use in the production of a series of individual absorbent articles, where the individual absorbent articles each define a pitch length in a machine direction and a maximum width in a cross direction. The substrate may be advanced past a printing station, where the printing station comprises a printing plate. A series of graphics can be printed the substrate at a first repeat pitch by repeatedly moving the printing plate into contact with the substrate, where consecutive graphics on the substrate are separated in the machine direction by a first repeat pitch distance. In one non-limiting embodiment, the substrate is activated to provide an activated region wherein the substrate is stretched in the cross direction to a width substantially equal to the maximum width of the individual absorbent articles. The substrate can be stretched in the machine direction to define a second repeat pitch distance separating consecutive graphics on the substrate, where the second repeat pitch distance is substantially equal to the pitch length of the individual absorbent articles.

In yet another non-limiting embodiment, a method for manufacturing absorbent articles having at least two different sizes is disclosed. In one non-limiting embodiment, a substrate is provided for use in the production of a first series of individual absorbent articles and second series of absorbent articles, where the individual absorbent articles of the first series each define a first pitch length in a machine direction and where the individual absorbent articles of the second series each define a second pitch length in a machine direction. The substrate can be fed onto a rotating central impression cylinder and moved past a printing station arranged adjacent an outer surface of the central impression cylinder, where the printing station comprises a printing plate. A series of graphics can be printed on the substrate by moving the printing plate into contact with the substrate, where consecutive graphics on the substrate are separated in the machine direction by a first repeat pitch distance substantially equal to the first pitch length. The substrate may be converted into one of a backsheet and a topsheet on the individual absorbent articles of the first series by activating the substrate to provide an activated region where the substrate is stretched in the machine direction to define a second repeat pitch distance separating consecutive graphics on the substrate, where second repeat pitch distance is substantially equal to the second pitch length. In one non-limiting embodiment, the activated substrate can be converted into one of a backsheet and a topsheet on the individual absorbent articles of the second series.

In yet another non-limiting embodiment, an absorbent article is produced with a substrate, where in accordance with the methods described in further detail below, the substrate has at least one graphic printed thereon and is subsequently activated.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIG. 3 is a top view of a substrate with a sample series of graphics printed thereon in accordance with one non-limiting embodiment.

FIG. 4 is a top view of a substrate with a sample series of graphics printed thereon in accordance with one non-limiting embodiment.

FIG. 10A-10C are teeth configurations in accordance with non-limiting embodiments.

DETAILED DESCRIPTION OF THE INVENTION

Figure 1B:
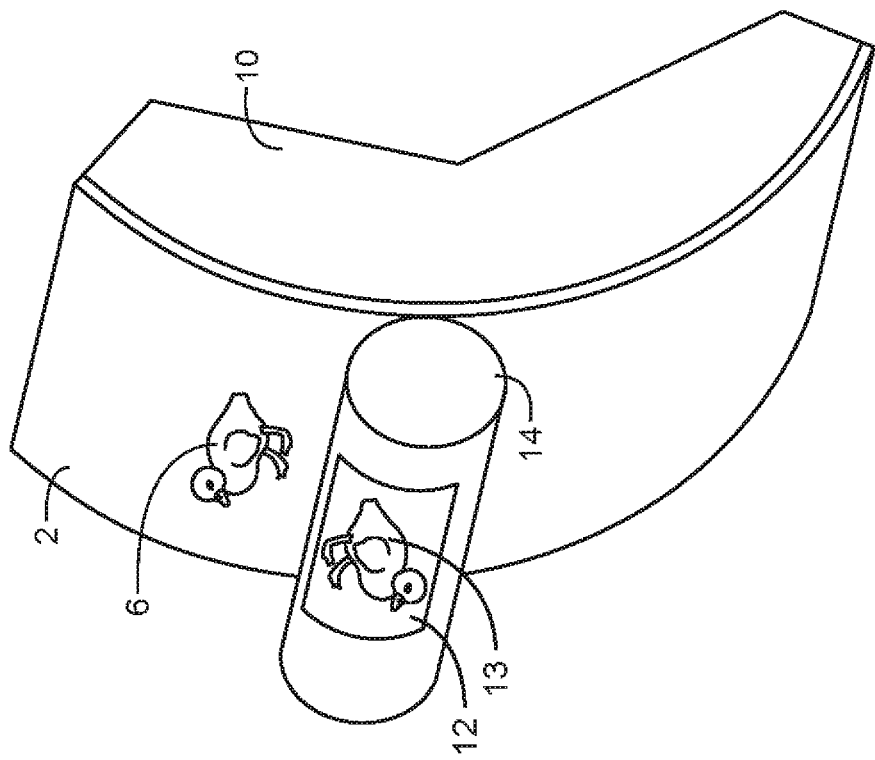
FIG. 1B is a detailed view of a printing unit of the printing machine of FIG. 1A in accordance with one non-limiting embodiment.

Various non-limiting embodiments of the present disclosure will now be described to provide an overall understanding of the principles of the structure, function, manufacture, and use of the systems, apparatuses, accessories, and methods disclosed herein. One or more examples of these non-limiting embodiments are illustrated in the accompanying drawings. It is to be appreciated that the systems, apparatuses, accessories, and methods specifically described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

Aspects of the present disclosure relate to printing and activating apparatuses and methods for printing a series of graphics on a substrate, and more particularly relate to apparatuses and methods for printing graphics with consecutive graphics separated in a machine direction by a first repeat pitch, activating the substrate to define a second repeat pitch separating the consecutive graphics on the substrate, and using the activated substrate in the production of absorbent articles. As discussed below, examples of such printed and activated substrates can be used in the manufacture of printed disposable diaper components, such as backsheets, topsheets, landing zones, fasteners, ears, absorbent cores, and acquisition layers, for example. Although the description below is mainly related to diaper components, it is to be appreciated that the apparatuses and methods described herein are also applicable to other types of absorbent articles, such as training and pull-up pants, incontinence briefs and undergarments, feminine hygiene garments, and cleaning and dusting devices, for example. As used herein, "machine direction" (MD) is used to refer to the direction of the material flow through a process. "Cross direction" (CD) is used herein to refer to a direction that is generally perpendicular to the machine direction.

As discussed in more detail below, a series of graphics may be printed on a substrate, wherein the repeat pitch distance is calibrated for use with a diaper of a first size. After the series of graphics is printed on the substrate, it may be incrementally stretched, or activated, in at least the machine direction. By activating the substrate in the machine direction, a second repeat pitch distance may be defined that is greater than the first repeat pitch distance. In other words, the distance between consecutive graphics on the substrate in the machine direction is increased. This second repeat pitch distance may be appropriately sized for a diaper of a second, larger size. As is to be appreciated upon consideration of the present disclosure, the amount of substrate activation may be varied so as allow absorbent articles of many different sizes to be produced from the substrate printed with graphics having a first repeat pitch distance. For example, the substrate may be activated to define a third repeat pitch distance that is greater than both the first repeat pitch distance and the second repeat distance. Therefore, as discussed in more detail below, a single printing process that prints graphics at a first repeat pitch distance may be used to print a substrate that will ultimately be used in the production of absorbent articles of varying sizes. Additionally, as discussed in more detail below, the substrate may also be activated in the cross direction to increase the width of the substrate in the cross direction.

In various embodiments, the substrate may be a material that is primarily two-dimensional (i.e., in an XY plane), the thickness (in a Z direction) of which is relatively small (i.e., 1/10 or less) in comparison to its length (in an X direction) and width (in a Y direction). Non-limiting examples of substrates include a layer or layers of fibrous materials, films and/or foils, such as plastic films or metallic foils that may be used alone or laminated to one or more webs, layers, films, and/or foils, for example. As such, a web is a substrate. Nonwoven materials may include materials made from continuous filaments or fibers and/or discontinuous filaments or fibers by processes such as spunbounding, meltblowing, and the like. Nonwovens do not typically have a woven or knitted filament pattern.

Figure 1A:
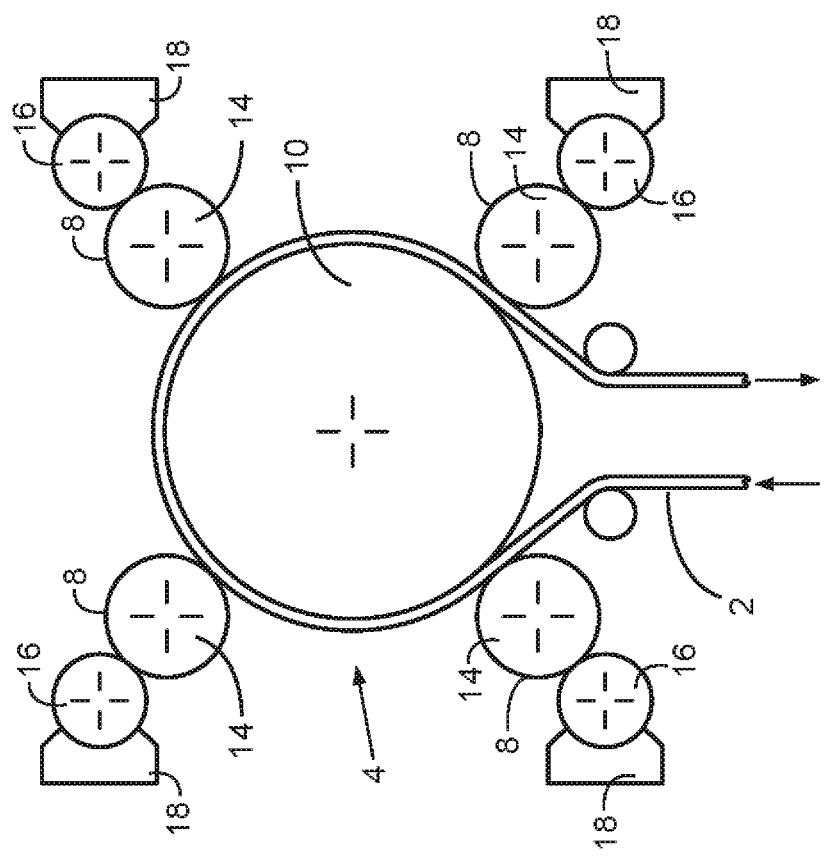
FIG. 1A is a printing machine in accordance with one non-limiting embodiment.

In one example embodiment, a conventional flexographic printing machine may be used to print a series of graphics on an advancing substrate. In conventional flexographic printing machines, such as shown in FIGS. 1A and 1B, a substrate 2 is fed into the printing machine 4 and an image 6 is printed as the substrate is advanced through a series of print units 8 disposed around a central impression cylinder 10. The print stations/units may be configured to print individual colors (such as cyan, magenta, yellow, and black) that make up the graphic image 6. Each print unit 8 may include a print plate 12 connected with the outer surface of print cylinder 14. The print plate 12 includes an image 13 of the graphic to be printed. The print stations also may include an anilox roll 16, which applies ink from an ink pan 18 to the print plate 12.

During the printing process, the central impression cylinder 10, the print cylinder 14, and anilox roll 16 all rotate, and the print plate 12 contacts the substrate 2 to transfer the ink from the graphic image 13 on the print plate 12 to the web, thereby printing a series of the graphic image 6 thereon. The print stations/units can be configured to print more than one image on the substrate by placing additional print plates on the print cylinder 14.

Figure 2B:
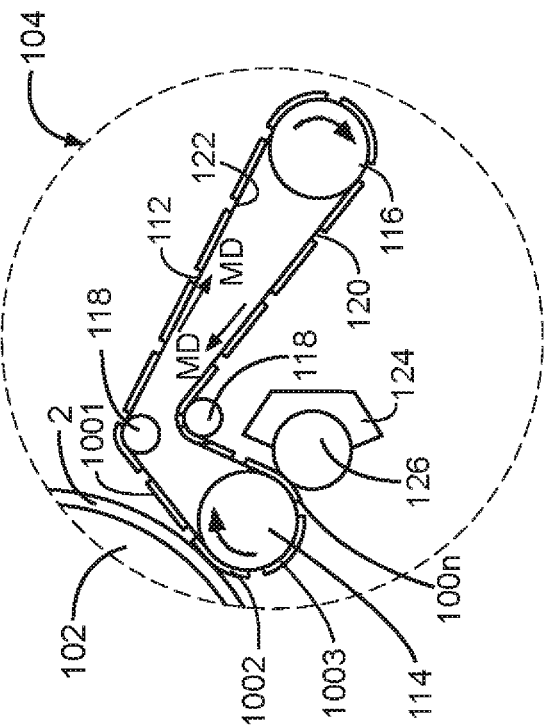
FIG. 2B is a detailed view of a printing station of the printing machine of FIG. 2A in accordance with one non-limiting embodiment.
Figure 2A:
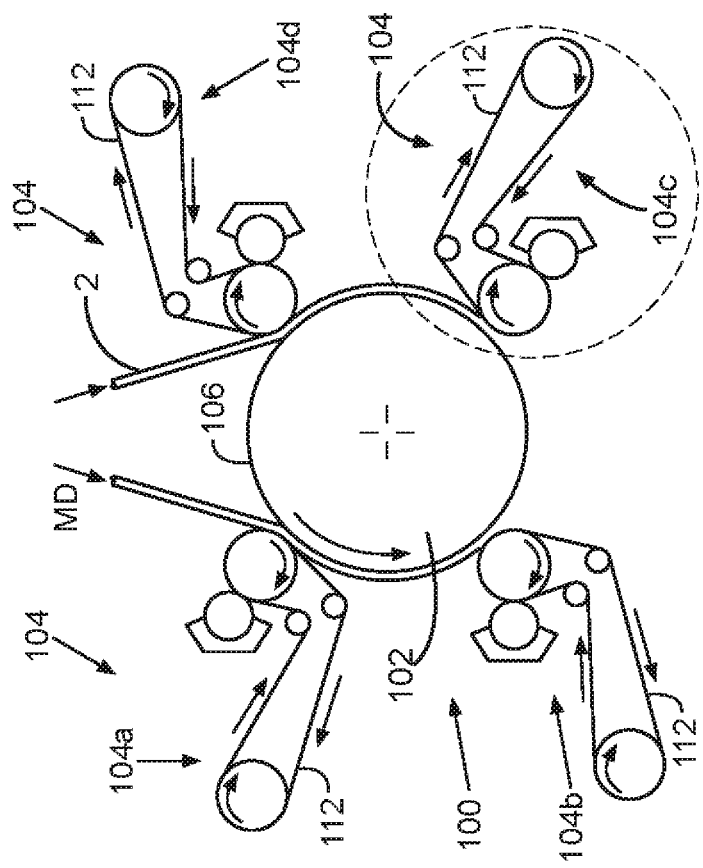
FIG. 2A is a printing machine in accordance with one non-limiting embodiment.

In another example embodiment, referring to FIGS. 2A and 2B, a printing apparatus 100 includes a central impression (CI) cylinder or CI drum 102 and a plurality of printing stations 104 disposed along an outer surface 106 of the central impression cylinder 102. Although the printing apparatus 100 illustrated in FIG. 2A includes four printing stations 104, it is to be appreciated that other embodiments may include more or less than four printing stations. During operation, the central impression cylinder 102 rotates in the direction shown and a substrate 2 is fed onto the rotating cylinder 102. The substrate 2 moves past each printing station 104 and exits the printing apparatus 100. As the substrate 2 moves past the printing stations 104, the printing stations 104 print a series of graphics on the substrate 108. As shown in FIG. 2B, each printing station 104 may include an endless belt 112 with a plurality of flexible printing plates (1001-100n) disposed thereon. In turn, the endless belt 112 is drawn around a first printing roller 114 and a second printing roller 116. As shown in FIG. 2B, the printing station 104 may also include one or more belt tensioning rollers 118 operably connected with endless belt 112 to help maintain a desired belt tension. The endless belt 112 has a first surface (or outer surface) 120 and a second surface (or inner surface) 122 opposite the first surface, wherein the printing plates (1001-100n) are disposed on the first surface 120, and wherein the second surface 122 is in contact with the first and second printing rollers 114, 116. The printing plates (1001-100n) may include printing patterns or graphics that are different from each other. During operation, the central impression cylinder 102 rotates and causes the endless belt 112 to advance and rotate the first and second print rollers 114, 116. As the endless belt 112 advances, the printing plates (1001-100n) on the endless belt 112 move into contact with the substrate 2 disposed on the rotating central drum 102. As the printing plates move into contact with the substrate, ink on the printing plates is transferred to the substrate 2.

As shown in FIG. 2B, each printing station 104 may also include an ink supply 124 and an anilox roller 126, which is operably connected with the ink supply 124 and the endless belt 112. During operation of the printing apparatus 100, the anilox roller 126 rotates and deposits ink from the ink supply 124 onto the printing plates (1001-100n) on the moving endless belt 112. The printing stations 104 may also include a device to remove excess ink from the anilox roller. For example, in some embodiments, the printing stations may include a doctor blade configured to scrape excess ink from the anilox roller before transferring ink to the printing plates (1001-100n). As the endless belt 112 advances, the printing plates (1001-100n) move into contact with the substrate 2 on the central drum 102, and in turn, transfer ink from the printing plate (1001-100n) to the substrate 2. Although not shown in FIG. 2B, it is to be appreciated that the printing stations 104 may also include ink dryers. Dryers located between printing stations may serve to partially dry the ink by a preceding print station, which may fix the ink from each preceding print station to the substrate and to help minimize ink smearing.

It is to be appreciated that a repeating series of graphics can be printed on a substrate using the printing machine 4, the printing apparatus 100, or any other suitable printing process, such as an ink jet printer, for example. Depending on the printing process used, a variety of unique graphics are available for printing on the substrate. Furthermore, the complexity or level of detail of the graphics may increase or decrease depending on the printing process used. While printing machine 4 is referenced in the various embodiments below, it is to be appreciated that this printing machine 4 is merely a representative example of an available printing technique and is not intended to limit the scope of the disclosure. Additional detailed descriptions of various printing machines can be found in EP 1 884 360, U.S. Pat. Nos. 5,010,817, and 6,811,239, for example.

An example printed substrate 2 is illustrated in FIGS. 3 and 4. In various embodiments, printed substrate 2 can be cut into individual components and/or combined with other substrates or components or otherwise modified during the manufacture of absorbent articles. Examples of such printed substrates can be used in the manufacture of printed diaper components, such as backsheets, topsheets, landing zones, fasteners, ears, absorbent cores, and acquisition layers, for example. In various embodiments, the substrate 2 is a continuous film material, for example, a breathable microporous polymer film, that is used as part of the diaper backsheet. It is to be appreciated that different printed diaper components may require different MD lengths. Table 1 below provides example MD lengths for various diaper components for different sized diapers:

|  | Backsheet, Outer Cover, Film, and Nonwoven Substrates | Topsheet, Nonwoven, and Liner Substrates |
| --- | --- | --- |
| Size 0 | 316 mm | 316 mm |
| Size 1 | 372 mm | 372 mm |
| Size 2 | 402 mm | 402 mm |
| Size 3 | 439 mm | 439 mm |
| Size 4 | 488 mm | 488 mm |
| Size 5 | 516 mm | 516 mm |
| Size 6 | 527 mm | 527 mm |
| Size 7 | 555 mm | 555 mm |
| Size 8 | 580 mm | 580 mm |
| Adult | 800 to 1000 mm | 800 to 1000 mm |

Referring to FIG. 3, substrate 2 has a repeating series of graphics (G1-Gn) printed on the substrate 2 along the machine direction. While the illustrated example embodiment shows a single repeated graphic (G1-Gn) printed on the substrate 2, it is to be appreciated that, in various embodiments, the substrate 2 may comprise multiple different graphics, patterns, colors, and/or shapes. The graphics (G1-Gn) are consecutively separated by a first repeat pitch distance (PD1). It is to be appreciated that the first repeat pitch distance is a function of, for example, the spacing of printing plate 12 on the printing unit 8 (FIGS. 1A and 1B) or the printing station 104 (FIGS. 2A and 2B). Once the graphics (G1-Gn) are printed on the substrate 2, the substrate 2 may be activated in the machine direction in order to generate an activated region and increase the repeat pitch distance. The activated region may be, for example, the entire length of the substrate 2, or the activated regions may be intermittently distributed along the length of the substrate 2. As described in further detail below, an MD activation apparatus 200 may be used to activate the substrate 2. For example, in one embodiment, a substrate 2 may be printed with graphics (G1-Gn) having a PD1 of about 372 mm, which corresponds to a length of a backsheet for a "Size 1" diaper. The substrate 2 may then be incrementally stretched, or activated, in the machine direction in order to increase the repeat pitch distance to about 402 mm. The activated substrate 2' with graphics (G1-Gn) having a second repeat pitch distance (PD2) can now be used in the production of "Size 2" diapers. The positioning of the graphics (G1-Gn) along the substrate 2 may be selected for proper placement on the backsheet with regard to the absorbent article to be subsequently produced. For example, in various embodiments, the graphics (G1-Gn) may be placed at a first repeat distance in order to position a graphic near a waistband of a subsequently produced absorbent article, such as a diaper, for example.

Referring to FIG. 4, the substrate 2, in addition to being activated in the machine direction, may also be activated in the cross direction. CD activation may serve to increase the width of the substrate in the cross direction. For example, the substrate 2 may have a cross direction width of CD1. After a CD activation process, the substrate 2' may have a cross direction of CD2. As described in further detail below, a CD activation apparatus 400 may be used to activate the substrate 2. It is to be appreciated that CD activation may not generally affect the repeat pitch distance of the graphics (G1-Gn). With the width of the substrate 2' incrementally increased, the substrate 2' may be useful in the production of larger absorbent articles. Furthermore, by activating the substrate 2' in the cross direction in conjunction with activating the substrate 2' in the machine direction, any potential distortion of the graphic in the machine direction through MD activation may be reduced or eliminated. More particularly, MD activation of a graphic causes the graphic to lengthen in the machine direction, which in turn, may cause the MD activated graphic to appear slightly distorted, as shown in FIG. 3. However, such distortion may be reduced by stretching the MD activated graphic in the CD direction, as shown in FIG. 4. In other words, a graphic having an aspect ratio may be subjected to both MD and CD activation to enlarge the graphic while maintaining substantially the same aspect ratio to reduce to eliminate a distorted appearance. As is to be appreciated, if CD activation of the substrate 2 is implemented in a production process, the CD activation may occur before or after the MD activation. Furthermore, if both CD and MD activation are implemented, the CD and MD activation may be part of the same "in-line" process, or the activation steps may be part of separate processes.

Figure 5B:
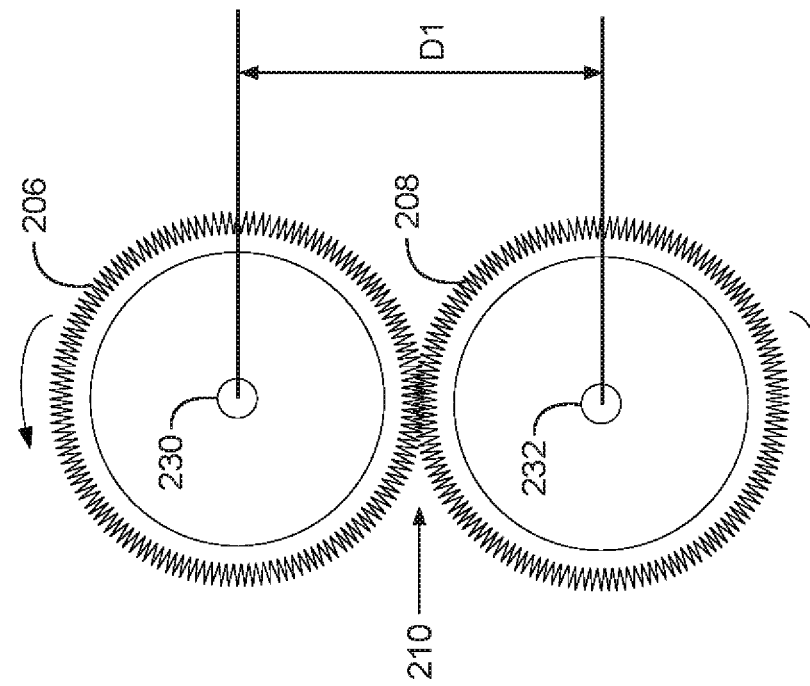
FIG. 5B is a cross-sectional view taken along line 5B-5B of FIG. 5A in accordance with one non-limiting embodiment.
Figure 5A:
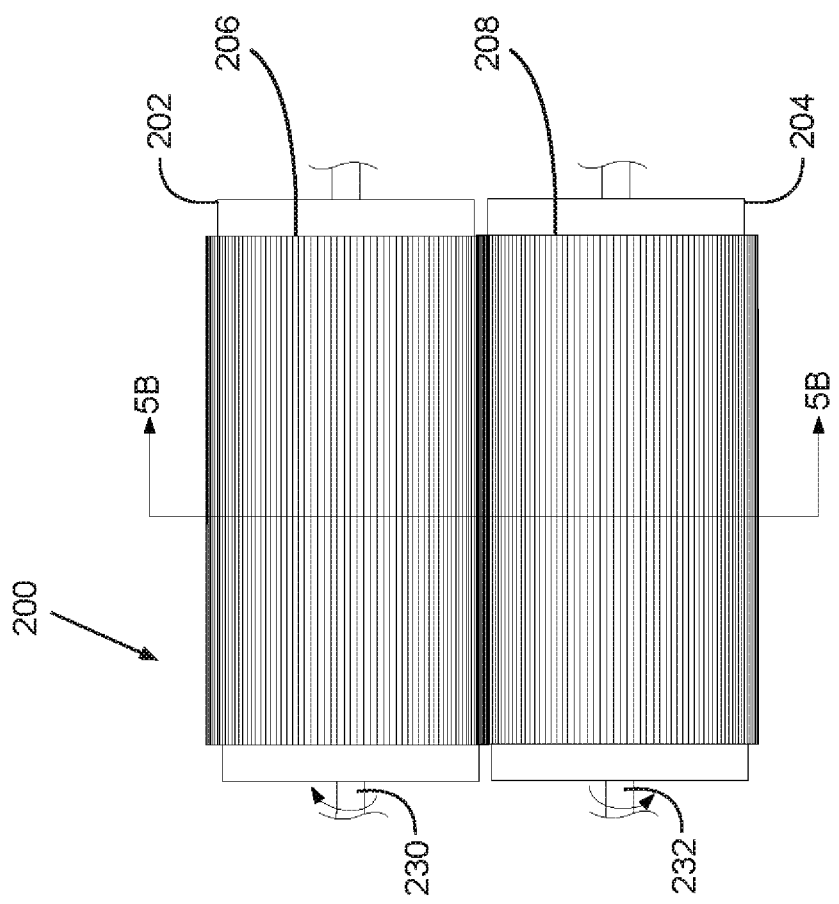
FIG. 5A is a side view of an activation apparatus in accordance with one non-limiting embodiment.
Figure 6:
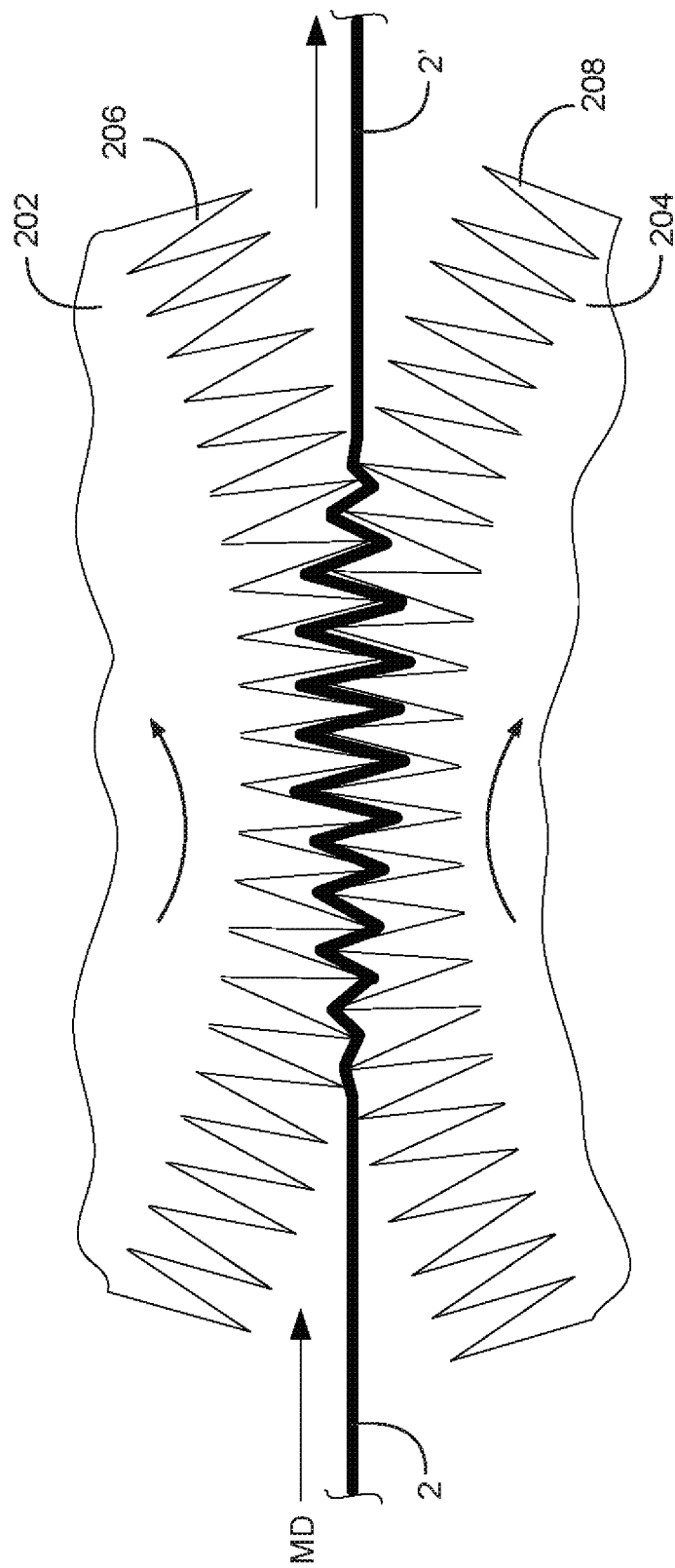
FIG. 6 is a detailed view of the activation apparatus of FIGS. 5A and 5B in accordance with one non-limiting embodiment.

In one embodiment, referring to FIGS. 5A, 5B, and 6, the MD activation apparatus 200 may comprise a first roller 202 and a second roller 204. The first roller 202 can have teeth 206 and the second roller 204 can have teeth 208. The first roller 202 may rotate about a shaft 230 and the second roller 204 may rotate about a shaft 232. The first roller 202 and the second roller 204 are configured to rotate at the same speed, or at substantially the same speed, and in opposite directions. In one embodiment, the rollers 202, 204 may rotate at about 400 RPM during the activation process. The rollers 202, 204 and teeth 206, 208 may be of any suitable size and material. In one embodiment, the first roller 202 and the second roller 204 may each have a diameter of about 300 mm and teeth 206, 208 may be about 10 mm deep, with the tips of consecutive teeth on the rollers 202, 204 separated by about 2 mm. It is to be appreciated that the diameter of the rollers may be varied depending on the tooth configuration and/or the size of the substrate being activated. As illustrated, the teeth 206, 208 may extend widthwise across the width of the rollers 202, 204; however, any suitable configuration of teeth may be used. For example, in some embodiments, the teeth 206 may not extend across the entire width of the first roller 202, thereby creating a gap or gaps around the entire circumference of the roller 202 or at least a portion of the circumference of the roller 202. It is to be appreciated that by forming a gap or gaps around the circumference of either one of the rollers 202, 204, various portions of the substrate 2 may be activated, while other portions of the substrate 2 may not be activated.

In one embodiment, referring to FIG. 6, as the first roller 202 and the second roller 204 rotate, teeth 206 and teeth 208 are configured to mesh with one another in a non-contacting engagement to form a nip 210. The rollers 202, 204 are configured so that contact is not made between the two sets of teeth. The teeth 202, 204 are slightly offset such that the teeth 206 on the first roller 202 are configured to be received by and mesh with the space adjacent two consecutive teeth 208 on the second roller 204. As the first roller 202 and the second roller 204 rotate, the substrate 2 is drawn through the nip 210 and the teeth 206 mesh with teeth 208. As the teeth 206, 208 mesh, the substrate 2 is engaged by the teeth 206, 208. As the substrate 2 passes through the nip 210, the substrate 2 is stretched over the teeth, as illustrated in FIG. 6. In various embodiments, the stretching first increases to a maximum level as the teeth 206, 208 continue to mesh and drive the substrate 2 between the consecutive teeth on the rollers. After maximum stretching of the substrate 2 has occurred, the teeth release the activated portion of substrate 2' as the rollers 202, 204 continue to rotate. The activate region of the substrate leaves the nip 210 in the machine direction.

While passing through the nip 210, the nonelastomeric substrate 2 is strained beyond its elastic limit to create plastically deformed areas of the substrate 2'. Therefore, the substrate 2' is essentially stretched or extended in the machine direction. Any graphics present on the activated region of substrate 2' are stretched or extended in the machine direction as well. It is to be appreciated that the amount of stretching achievable for any particular substrate depends upon, among other factors, the deformation curve of the material. For example, various materials may have higher elastic properties and require a relatively large amount of stretching in order to plastically deform the substrate. Other materials, however, would tear at the same levels of stretching.

Figure 7A:
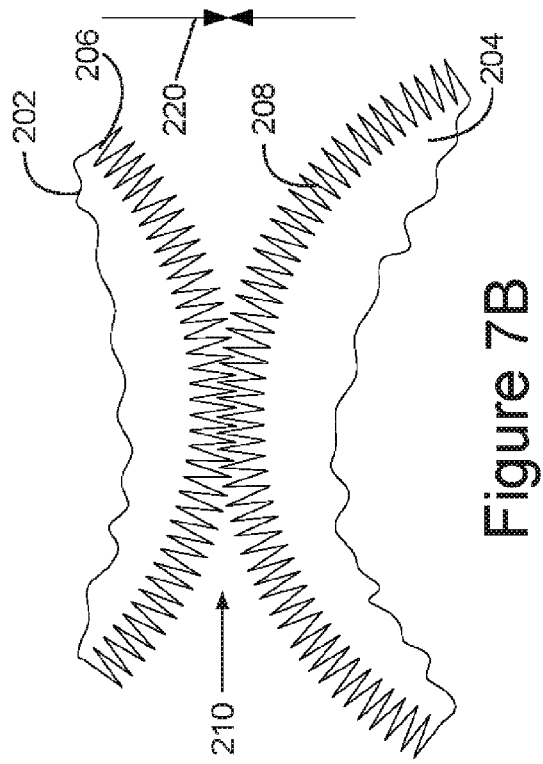
FIGS. 7A-7C are detailed views of the activation apparatus of FIGS. 5A and 5B with varying center-to-center distances in accordance with non-limiting embodiments.
Figure 7B:
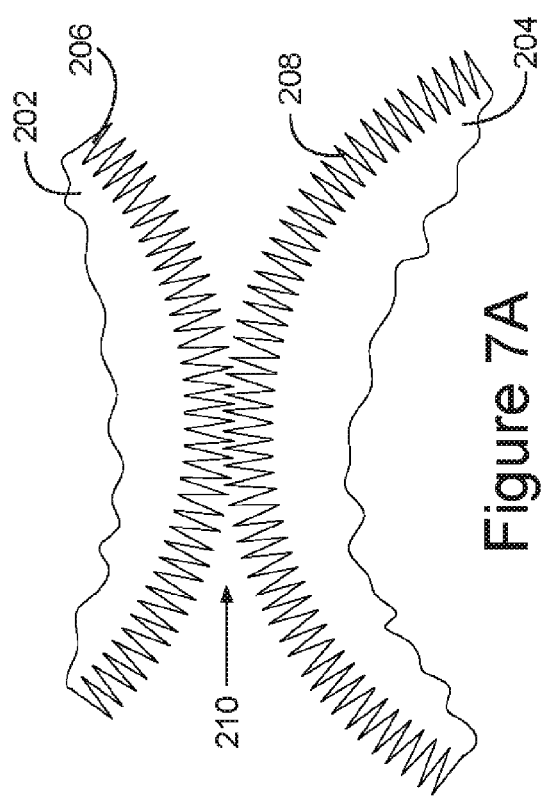
Figure 7C:
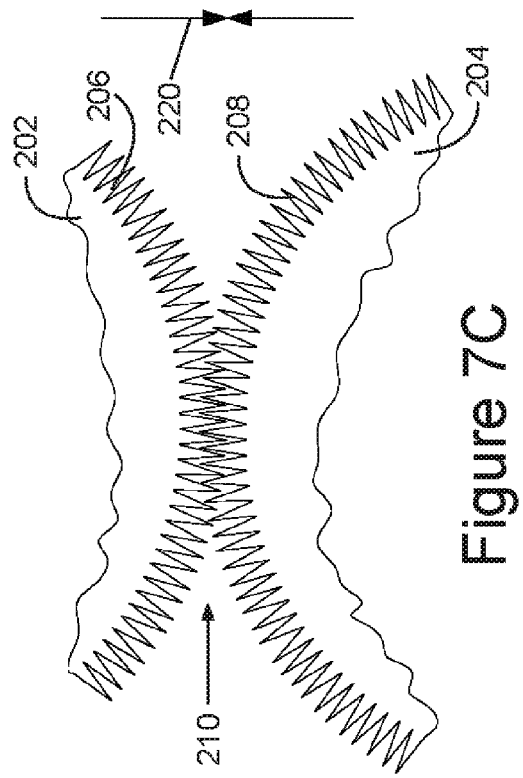

In one embodiment, referring to FIGS. 7A, 7B, and 7C, the center-to-center distance ($D_1$) (FIG. 5B) of the first roller 202 and the second roller 204 may be selectively adjusted. By selectively adjusting $D_1$, the amount of teeth overlap in the nip 210, or the amount of engagement between the teeth 206 on roller 202 and the teeth 204 on roller 206, may be altered. As the amount of teeth overlap increases, the substrate 2 experiences a greater amount of stretching while passing through the nip 210, thereby increasing the amount of activation the substrate 2' experiences. Accordingly, in various embodiments, the substrate 2, printed with graphics (G1-Gn) at a first repeat pitch length, can be activated with the configuration illustrated in FIG. 7A to define a second repeat pitch length on the substrate 2'. The rollers 202, 204 may then be moved toward each other, as indicated by arrows 220, to increase the teeth overlap in the nip 210. The substrate 2, printed with graphics (G1-Gn) at a first repeat pitch length, can then be activated with the configuration illustrated in FIG. 7B to define a third repeat pitch distance on the substrate 2'. The rollers 202, 204 may then again be moved toward each other, as indicated by arrows 220, to further increase the teeth overlap in the nip 210. The substrate 2, printed with graphics (G1-Gn) at a first repeat pitch length, can be activated with the configuration illustrated in FIG. 7C to define a fourth repeat pitch distance on the substrate 2'. Through adjustment of the center-to-center distance of the first roller 202 and the second roller 204, the amount of activation of the substrate 2 can be altered or varied. In various embodiments, the adjustment of the center-to-center distance of the rollers may be performed automatically or manually. It is to be appreciated that by separating the rollers 202, 204 by a distance $D_1$ such that there is no teeth overlap in the nip 210, the activation apparatus 200 may be selectively engaged and disengaged from the substrate 2.

In one embodiment, a substrate 2 having a first repeat pitch distance calibrated for use with a first diaper size, may be fed through the rollers illustrated in FIG. 7A in order to create a substrate 2' that is suitable for use with a second, larger diaper size. The substrate 2 having a first repeat pitch distance calibrated for use with a first diaper size, may be fed through the same rollers but with a different offset distance (FIG. 7B) to create a substrate 2' that is suitable for use with a third diaper size. The substrate 2 also may be fed through the same rollers but configured with a shorter offset distance (FIG. 7D) to create a substrate 2' that is suitable for use with a fourth diaper size, which would be a larger diaper size than the other three diapers. While three selectable roller offset distances are illustrated in FIGS. 7A, 7B, and 7C, it is appreciated that through incremental changes in the roller offset distance, the roller offset distance may be configured to any suitable level.

Figure 8B:
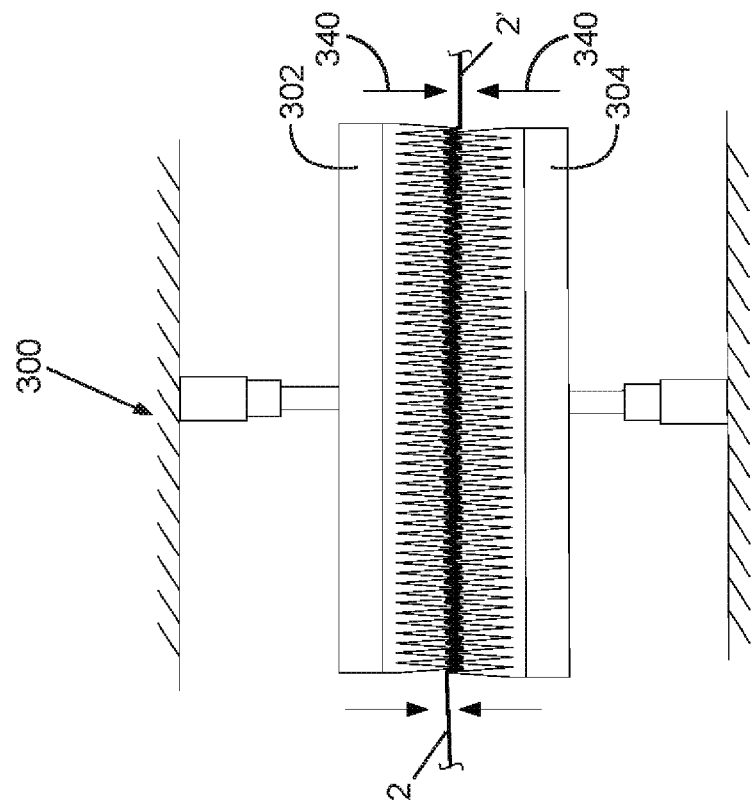
FIGS. 8A-8B are a stamping activation apparatus in accordance with one non-limiting embodiment.
Figure 8A:
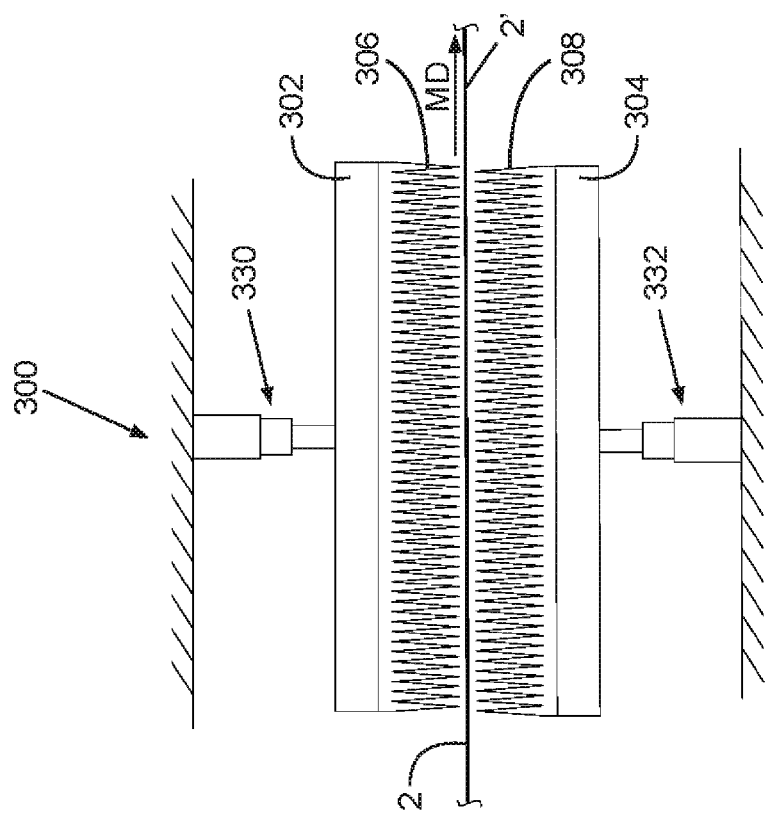

In one alternative embodiment, referring to FIGS. 8A and 8B, an activation stamping apparatus 300 may be used to activate the substrate 2. In one embodiment, the activation stamping apparatus 300 may comprise a first plate 302 and a second plate 304. The first plate 302 can have teeth 306 and the second plate 304 can have teeth 308. While the illustrated embodiment comprises teeth 306, 308 covering essentially the entire plates 302, 304, it is appreciated that the teeth 306, 308 may only cover select portions of the plates 302, 304, for example. The first plate 302 may be operably connected with a drive mechanism, such as first piston 330, and the second plate 304 may be operably connected with a drive mechanism, such as a second piston 332. It is to be appreciated that any suitable drive mechanism may be used to operate the activation stamping apparatus 300. During operation, the substrate 2 can be fed intermediate the top plate 302 and the bottom plate 304. When the substrate 2 has stopped, the pistons 330, 332 can drive the plates together, as indicated by arrows 340. As previously described, the teeth 306 and 308, which are configured to mesh in a non-contacting engagement, stretch the substrate 2 between the teeth 306 and 308. It is to be appreciated that the amount the substrate 2' is stretched may be varied based on how close the top plate 302 and the bottom plate 304 are driven together. In one embodiment, the amount of teeth overlap is relatively small, thereby resulting in less activation of the substrate 2'. In another embodiment, the teeth overlap is greater, thereby resulting in a greater activation of the substrate 2'.

Figure 9B:
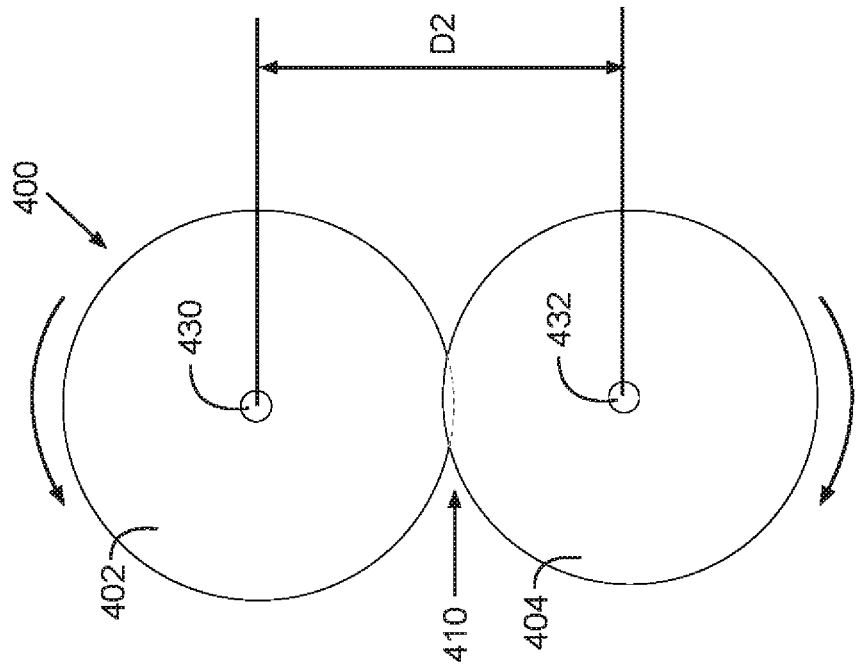
FIG. 9B is a cross-sectional view taken along line 9B-9B of FIG. 9 in accordance with one non-limiting embodiment.
Figure 9A:
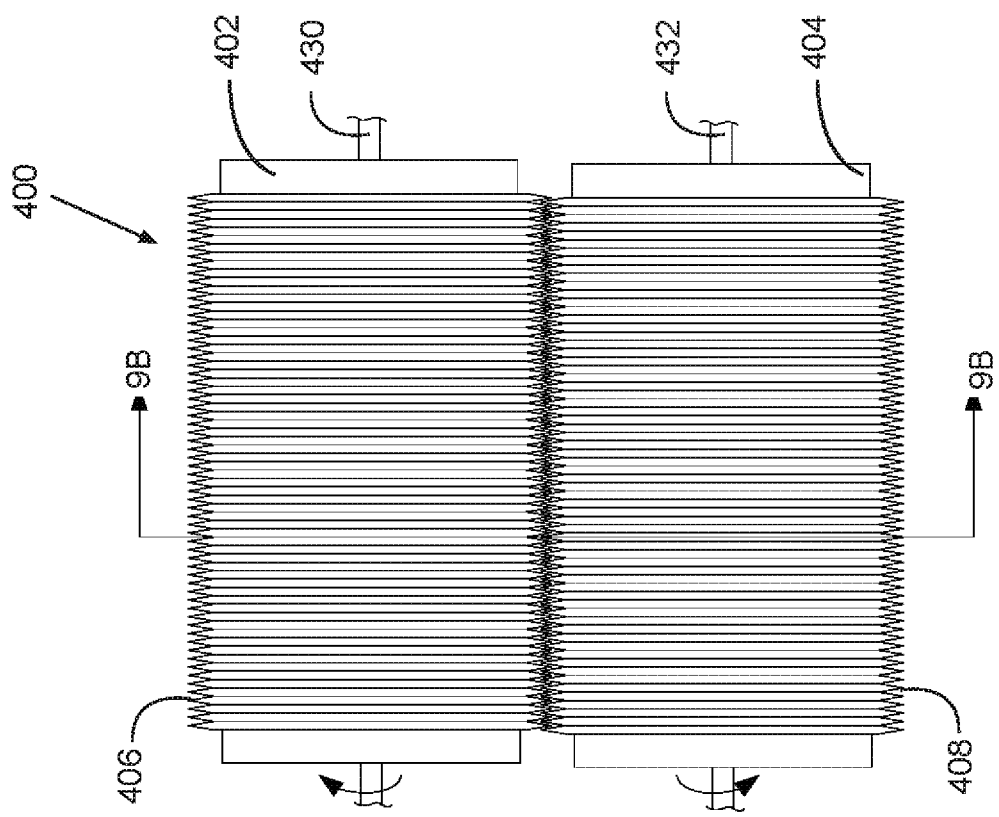
FIG. 9A is a side view of an activation apparatus in accordance with one non-limiting embodiment.

In one embodiment, referring to FIGS. 9A and 9B, the CD activation apparatus 400 may comprise a first roller 402 and a second roller 404. The first roller 402 can have teeth 406 and the second roller 404 can have teeth 408. The first roller 402 may rotate about a shaft 430 and the second roller 404 may rotate about a shaft 432. The first roller 402 and the second roller 404 are configured to rotate at the same speed, or substantially the same speed, and in opposite directions. In one embodiment, the rollers 402, 404 may rotate at about 400 RPM. The rollers 402, 404 and the teeth 406, 408 may be of any suitable size. In one embodiment, the first roller 402 and the second roller 404 may each have a diameter of about 300 mm and teeth 406, 408 may be about 10 mm deep, with the tips of consecutive teeth on the rollers 402, 404 separated by about 2 mm. It is to be appreciated that the diameter of the rollers may be varied depending on the tooth configuration and/or the size of the substrate being activated. As illustrated, the teeth 406, 408 may extend around the entire circumference of the rollers 402, 404; however, any suitable configuration of teeth may also be used. For example, in some embodiments, the teeth 406 may not extend around the entire circumference of the roller 402 and instead a gap, or a plurality of gaps, is formed on the roller 402. It is to be appreciated that by forming a gap or gaps around the circumference of either one of the rollers 402, 404, various portions of the substrate 2' may be activated, while other portions of the substrate 2 may not be activated.

In one embodiment, referring to FIG. 9B, the teeth 406 and the teeth 408 are configured to engage or mesh with one another to form a nip 410. It is to be appreciated that the rollers 402, 404 are configured so that contact is not made between the two sets of teeth during engagement. Instead, teeth 406 on the first roller 402 are configured to mesh with and be received by the space adjacent two consecutive teeth 408 on the second roller 404. As the first roller 402 and the second roller 404 rotate, the substrate 2 is drawn into the nip 410 and the teeth 406 mesh with teeth 408. As the teeth 406, 408 mesh, the substrate 2 is engaged by the teeth 406, 408 and stretched over the teeth, as previously described with regard to other embodiments. Similar to the previously described embodiments, the center-to-center distance ($D_2$) (FIG. 9B) of the roller 402 and the roller 404 may be adjusted in order to alter the magnitude of activation in the cross direction.

Similar to the previously discussed embodiments, while passing through the nip 410, the nonelastomeric substrate 2 is strained beyond its elastic limit to create plastically deformed areas of the substrate 2'. Therefore, the substrate 2' is essentially stretched in the cross direction. It is to be appreciated that the amount of stretching achievable in the cross direction for any particular substrate depends upon, among other factors, the deformation curve of the material. For example, various materials may have higher elastic properties and require a relatively large amount of stretching in order to plastically deform the substrate. Other materials, however, would tear at the same levels of stretching.

As will be appreciated upon consideration of the present disclosure, a stamping apparatus similar to the stamping apparatus 300 may be used to activate the substrate 2 in the cross direction. In order implement a stamping apparatus configuration 300 for cross direction activation, the teeth in the stamping apparatus machine extend generally parallel to the machine direction. As is to be appreciated, a series of stamping apparatuses 300 can be implanted, each with teeth in various configurations allowing various portions of the substrate 2' to be activated.

The design of the teeth present on the rollers 202, 204, 402, 404 and stamp activation apparatuses 300 may vary in design. For illustration purposes, a portion of teeth 206, 208 are illustrated in FIG. 10A. The teeth 206, 208 may have inwardly tapered sides that join at the top of each tooth. A top portion of the tooth 207, 209 may be configured to avoid cutting or puncturing of the substrate 2 during the activation process. In one embodiment, for example, the top portion of the teeth 207, 209 are rounded or blunt to aid in the handling of the substrate 2. In one embodiment, referring to FIG. 10B, the teeth 206', 208' may have generally parallel sides. As illustrated in FIG. 10C, the teeth 206", 208", may have generally parallel sides with the top of the tooth rounded or blunt to avoid damaging the substrate 2. It is to be appreciated that any suitable teeth configuration, or combination of multiple teeth configurations, can be implemented for the activation process.

It is to be appreciated that various types of activation methods and apparatuses may be used in accordance with the present disclosure. For example, additional detailed descriptions of various types of MD and CD activation methods and apparatuses can be found in U.S. Pat. Nos. 6,120,632, 6,500,377, and 7,368,027.

In various embodiments, referring to FIGS. 11 through 14, the printing and activation process may be configured in a variety of implementations. While FIGS. 11 to 14 illustrate various non-limiting embodiments of a printing and activation process, It is to be appreciated that any suitable combination of printing and activation steps may be implemented. The activation processes may be cross direction activation, machine direction activation, or a combination of both, for example. Furthermore, while not illustrated, other components or processes may be incorporated into various embodiments of the present disclosure, such as ink dryers, belt tensioners, glue applicators, ultrasonic bonders, and cutter/trimmers, for example. In various embodiments, the printing apparatuses and methods may be an offline printing process (i.e., the printing process is not part of the absorbent article manufacturing process). In other embodiments, the printing apparatuses and methods may be applicable as an online process. In various embodiments, the activating apparatuses and methods may be an offline printing process. In other embodiments, the activating apparatuses and methods may be applicable as an online process. As discussed above, the printing and activation process disclosed herein may be used in a process to manufacture absorbent products using a substrate printed with graphics at a first repeat pitch distance that is too short for the finished absorbent product. Furthermore, the substrate may be originally too narrow for use with the finished absorbent article. Through at least one activation process, the substrate can be activated to adjust the spacing of the graphics on the substrate to make the substrate compatible with larger-sized absorbent articles.

Figure 11:
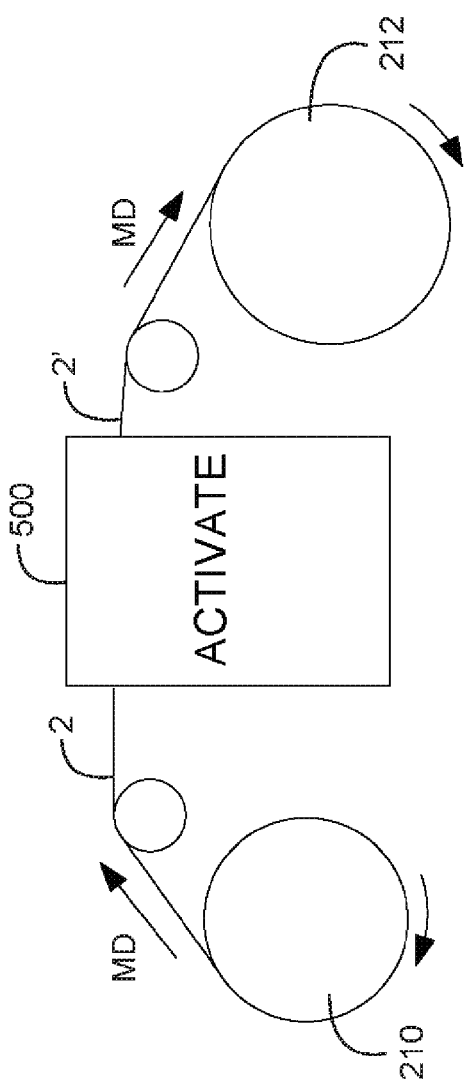
FIGS. 11-14 are schematic diagrams showing printing and activation processes in accordance with non-limiting embodiments.

In one embodiment, referring to FIG. 11, a roll 210 of the substrate 2 may be activated by an activation apparatus 500. In this embodiment, the substrate 2 may have had a series of graphics previously printed on the substrate 2. The series of graphics may be printed on the substrate 2 with a first repeat pitch distance. Once activated, the activated substrate 2' may be rolled onto a spool 212. The series of graphics on the substrate 2' rolled on the spool 212 may have a second repeat pitch distance. Spool 212 may then be used in the assembly process of an absorbent article. As previously discussed, the difference in length between the first repeat pitch distance and the second repeat pitch distance may be defined by the activation process. It is to be appreciated that the activation apparatus 500 can be any suitable activation process, such as an MD activation apparatus 200, a CD activation apparatus 400, or a combination of both, for example. The activation apparatus 500 may activate the entire substrate 2 or a portion of substrate 2. Furthermore, the activation apparatus 500 may comprise a series of rollers, one or more stamping arrangements, or a combination of both, for example.

Figure 12:
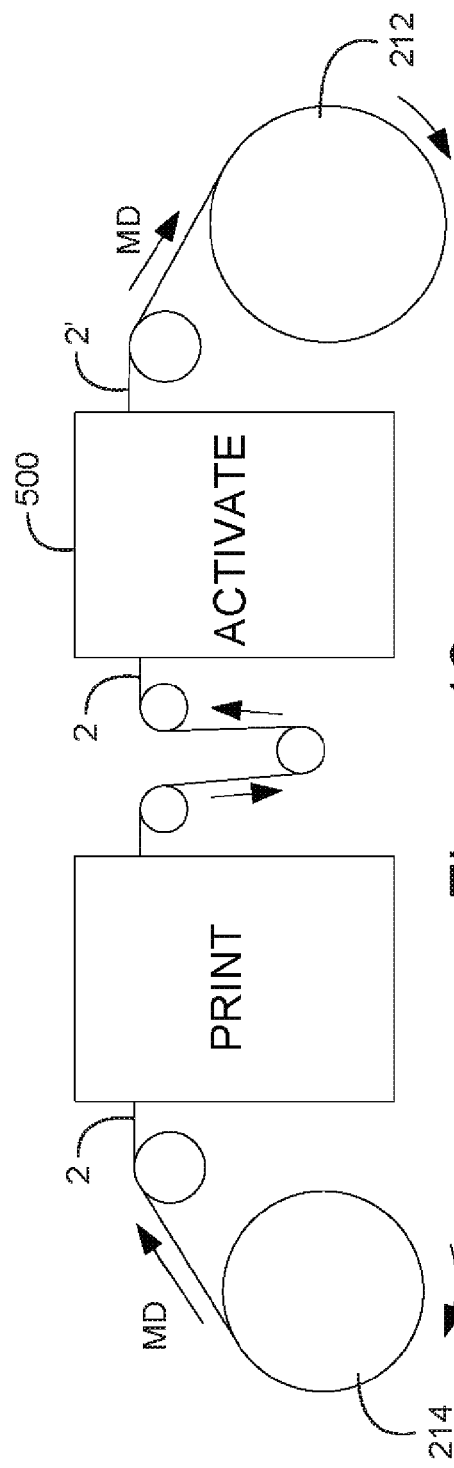

In one embodiment, referring to FIG. 12, the substrate 2 may be fed from a roll 214 into a printing machine 4. A series of graphics may be printed onto the substrate 2 using any suitable printing technique, such as flexographic printing, for example. In the illustrated embodiment, once printed, the substrate may be fed into the activation apparatus 500. Once the substrate 2 is activated with the activation apparatus 500, the substrate 2' may be rolled onto the spool 212. The spool 212 may then be used in the assembly process of an absorbent article.

Figure 13:
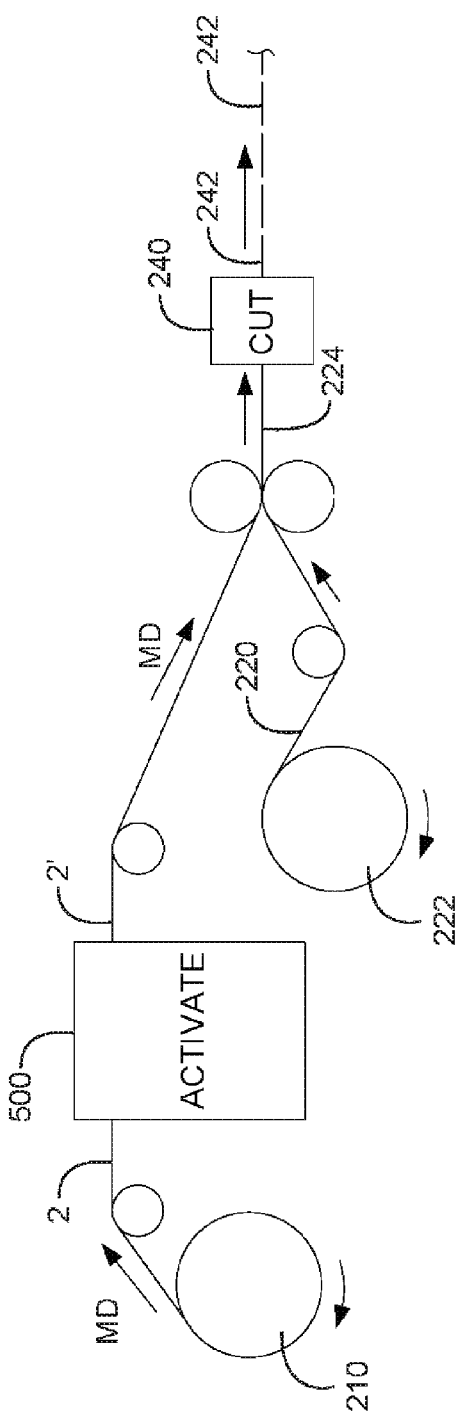

In one embodiment, referring to FIG. 13, a roll 210 of the substrate 2 may be activated by an activation apparatus 500. Once activated, the substrate 2' may be joined with a material 220. While the material 220 is illustrated as a single layer wound on a spool 222, it is to be appreciated that material 220 may comprise a plurality of different layers and materials, such as a topsheet layer and an absorbent layer, for example, each of which is described in further detail below. Once the substrate 2 is joined with the material 220 (i.e., adhesively joined or ultrasonically joined), a multi-layer substrate 224 can be formed. In one embodiment, the substrate 2 is a backsheet of the multi-layer substrate 224. It is to be appreciated that other layers, such as a fibrous layer (not illustrated) may be placed over the top of the backsheet. The multi-layer substrate 224 may be fed into a cutting apparatus 240 and cut or severed into individual absorbent articles 242. The length of the individual absorbent articles in the machine direction may vary depending on the size of the absorbent article being produced with the process. In one example embodiment, a Size 2 diaper measuring about 402 mm in the machine direction may be produced. Therefore, the cutting apparatus cuts the multi-layer substrate 224 approximately every 402 mm. In another example embodiment, a Size 5 diaper measuring about 516 mm in the machine direction may be produced. Therefore, the cutting apparatus cuts the multi-layer substrate 224 approximately every 516 mm. It is to be appreciated that upon consideration of the present disclosure, absorbent articles of varying sizes may be produced from a substrate initially having graphics printed at a single repeat pitch length, such as a repeat pitch length compatible with Size 1 diapers, for example.

Figure 14:
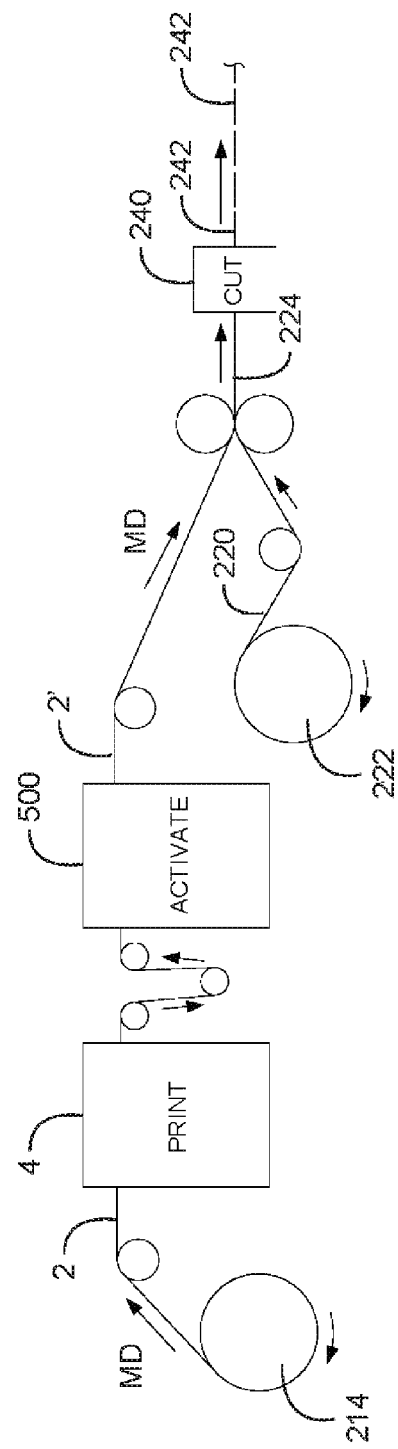

In one embodiment, referring to FIG. 14, the substrate 2 may be fed from a roll 214 into a printing machine 4. A series of graphics may be printed onto the substrate 2 using any suitable printing technique, such as flexographic printing, for example. The substrate 2 may then be fed into the activation apparatus 500 and activated by the activation apparatus 500. Once activated, the substrate 2' may be joined with a material 220. Once the substrate 2' is joined with the material 220, a multi-layer substrate 224 can be formed. In one embodiment, the multi-layer substrate 224 may be fed into the cutting apparatus 240 and cut or severed into individual absorbent articles 242. In one embodiment, the activated substrate 2' may be cut or severed to create individual components prior to being joined with the material 220.

Figure 15B:
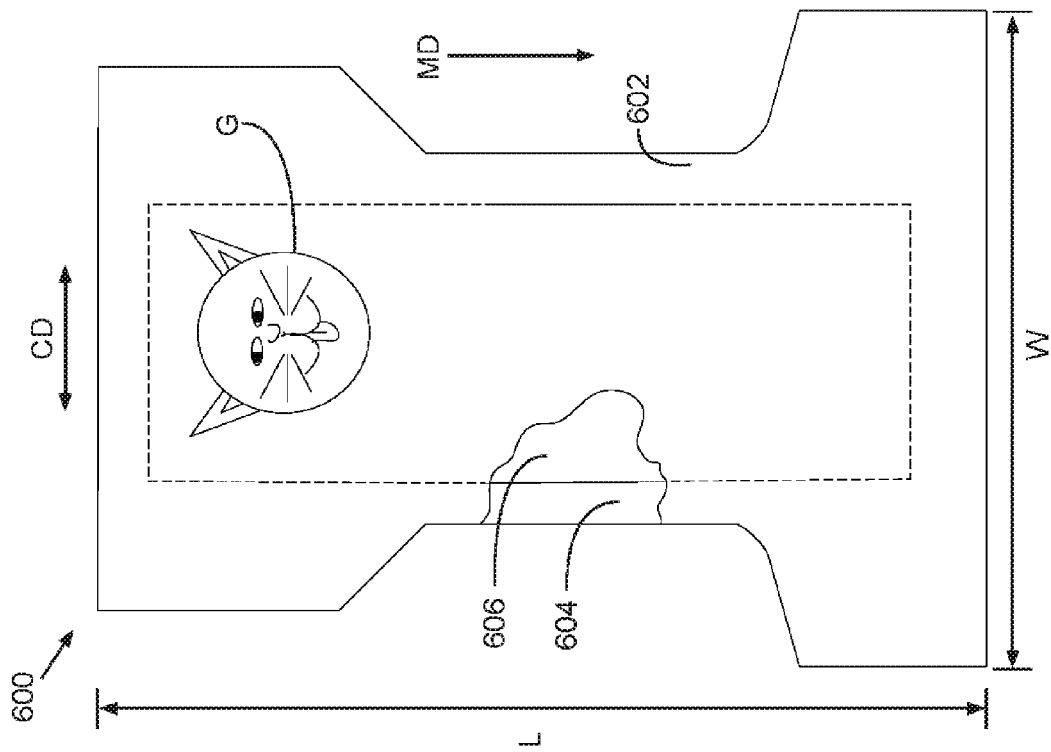
FIG. 15B is a plan view of the example absorbent article of FIG. 15A in accordance with one non-limiting embodiment.
Figure 15A:
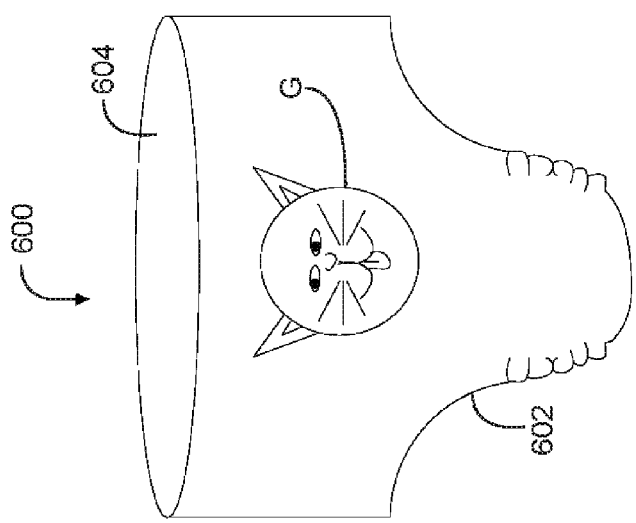
FIG. 15A is a front view of an example absorbent article in accordance with one non-limiting embodiment.

As shown in FIGS. 15A and 15B, absorbent articles, such as a diaper 600, for example, may be produced using the apparatuses and methods disclosed herein. In one embodiment, the diaper 600 can generally be comprised of a backsheet 602, a topsheet 604, and an absorbent layer 606 (shown in dashed lines in FIG. 15B) located between the backsheet 602 and the topsheet 604. The backsheet 602 is the surface which faces away from the wearer's body, while the topsheet 604 is the surface which faces towards the wearer's body. As illustrated, the diaper 600 has a pitch length of "L" in the machine direction. As discussed above, the pitch length L may vary depending the size of the absorbent article being produced. In various embodiments, the pitch length may vary between about 300 mm and about 1000 mm, depending on the type of product being produced. It is to be appreciated that depending on the product, the pitch length may be less than about 300 mm or greater than about 1000 mm. As discussed in further detail above, a substrate 2 of the backsheet 602 may be printed with graphics having a first repeat pitch distance that is less than or shorter than the pitch length L. After MD activation, the repeat pitch distance of the backsheet 602 may be substantially equal to the pitch length of the individual absorbent article in order to have proper placement of the graphics upon the individual articles. For example, the individual absorbent article may have a pitch length of about 480 mm and the repeat pitch distance of the backsheet 602 subsequent to MD activation may be in the range of about 460 mm to 490 mm. In one embodiment, the individual absorbent article may have a pitch length of 480 mm and the repeat pitch distance of the backsheet 602 subsequent to MD activation may be about 475 mm. Furthermore, as illustrated, the diaper 600 has a maximum width of "W" in the machine direction. The width "W" may vary depending on the size of the absorbent article being produced. As discussed in further detail above, the substrate 2 of the backsheet 602 may originally have a width in the cross direction that is less than or shorter than the maximum width "W". Through the activation processes described herein, the width of the backsheet 602 can be increased through CD activation so that it is substantially equal to the maximum width "W". In some embodiments, the width of the backsheet 602 is be increased through CD activation and still remain substantially less than the maximum width "W".

In various embodiments, the backsheet 602 may be formed by only one sheet (or layer) of material such as a breathable (or microporous) film material or a non-breathable (or non-microporous) film material. In some embodiments, the backsheet 602 may be formed by two (or more) sheet (or layer) materials, which may include a non-breathable or breathable film material and a nonwoven outer cover material. In some embodiments, the backsheet 602 may be formed by a laminate of two sheet (or layer) materials joined together, for example. The backsheet 602 may include a non-breathable film material and a nonwoven material, which is joined to the garment facing surface of the film material to provide a cloth-like and/or garment-like feel. In one embodiment, the nonwoven material is joined to the backsheet 602 after the backsheet 602 has been activated. In other embodiments, the backsheet 602 and the nonwoven material are activated subsequent to being joined. In one embodiment the backsheet 602 is impervious to liquids (e.g., urine) and comprises a thin plastic film such as thermoplastic film having a thickness of about 0.012 mm to about 0.051 mm. In one embodiment, the backsheet is a microporous polymer film formed from a mixture of polyethylene and calcium carbonate, and titanium dioxide, if needed, to increase the white appearance of the film. In accordance with the discussion above, graphics may be printed on a substrate to make printed component material, which may be converted into printed components to manufacture the backsheet 602. In some arrangements, the graphics may be covered or protected by the nonwoven material, wherein the graphics are visible through the nonwoven material. Thus, the substrate may be in the form of a film material and/or nonwoven material used to construct the backsheet 602.

In one embodiment, graphics may be printed on a substrate used as a printed component material to construct the topsheet 604. As such, graphics (G1-Gn) may be printed on any surface of the component material(s) of the topsheet 604 at a first repeat pitch distance. The component materials may be then be activated in accordance with the present disclosure to increase the repeat pitch distance. The topsheet 604 may be constructed to be compliant, soft-feeling, and non-irritating to the wearer's skin. Further, at least a portion of the topsheet 604 may be liquid pervious, permitting liquid to readily penetrate therethrough. As such, the topsheet 604 may be manufactured from a wide range of materials, such as porous foams, reticulated foams, apertured nonwovens or plastic films, or woven or nonwoven webs of natural fibers (e.g., wood or cotton fibers), synthetic fibers (e.g., polyester, polyethylene, or polypropylene fibers), or a combination of natural and synthetic fibers, for example. If the absorbent assemblies include fibers, the fibers may be spunbounded, carded, wet-laid, meltblown, hydroentangled, for example, or otherwise processed using any other suitable techniques.

In some embodiments, the topsheet 604 is made of a hydrophobic material or is treated to be hydrophobic in order to isolate the wearer's skin from liquids contained in the absorbent core. If the topsheet 604 is made of a hydrophobic material, at least the upper surface of the topsheet 604 may be treated to be hydrophilic so that liquids will transfer through the topsheet 604 more rapidly. This quality diminishes the likelihood that body exudates will flow off the topsheet rather than being drawn through the topsheet 604 and being absorbed by the absorbent layer 606. The topsheet 604 can be rendered hydrophilic by treating it with a surfactant or by incorporating a surfactant into the topsheet 604. Suitable methods for treating the topsheet 604 with a surfactant include spraying the topsheet material with the surfactant and immersing the material into the surfactant.

In one embodiment, the absorbent layer 606 is made from material that is generally compressible, conformable, non-irritating to the wearer's skin, and/or capable of absorbing and retaining liquids such as urine and other body exudates, for example. Thus, in addition to the backsheet 602 and the topsheet 604 components, it should be appreciated that graphics may be printed on substrates used as printed component material to construct the absorbent layer 606 and the printed component material may be subsequently activated to alter its width and/or length. The absorbent layer 606 and/or core can be manufactured in a wide variety of sizes and/or shapes, such as rectangular, hourglass, T-shaped, and asymmetric, for example. The absorbent layer 606 may also include a wide variety of liquid-absorbent materials commonly used in disposable diapers and other absorbent articles. In one example embodiment, the absorbent layer 606 may include comminuted wood pulp, which is generally referred to as airfelt. Examples of other absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any known absorbent materials or combinations of materials. It is to be appreciated that the configuration and construction of the absorbent layer 606 may be varied (e.g., the absorbent core(s) or other absorbent structure(s) may have varying caliper zones, a hydrophilic gradient, a superabsorbent gradient, or lower average density and lower average basis weight acquisition zones, or may comprise one or more layers or structures).

The absorbent articles, such as disposable diapers, for example, produced according the present disclosure can also include other features such as elastically extensible side panels. The side panels may be joined at seams to form waist opening and leg openings. The diapers may also include leg elastics and an elastic waist region to enhance the fits around the legs and waist of the wearer. In addition to the backsheet, topsheet, absorbent core, acquisition layer, and other diaper components, graphics may be printed on substrates used as printed component material to construct the fastening elements on the diaper, such as hook and loop fasteners and adhesive tabs, for example.

It is to be appreciated that upon consideration of the present disclosure, various portions of the substrate may be activated, while other portions of the substrate may remain un-activated. In one embodiment, the portion of the substrate covered by a graphic remains un-activated. In another embodiment, the portion of the substrate generally covered by the graphic may be activated. In another embodiment, the entire substrate may be activated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manufacturing absorbent articles having at least two different sizes comprising the steps of:
   providing a substrate used in the production of a first series of individual absorbent articles and second series of absorbent articles, wherein the individual absorbent articles of the first series each define a first pitch length in a machine direction, and wherein the individual absorbent articles of the second series each define a second pitch length in a machine direction, wherein the second pitch length is different from the first pitch length;
   feeding the substrate onto a rotating central impression cylinder;
   moving the substrate past a printing station arranged adjacent to an outer surface of the central impression cylinder, wherein the printing station comprises a printing plate;
   printing a series of graphics on the substrate by moving the printing plate into contact with the substrate, wherein consecutive graphics of the series of graphics on the substrate are separated in the machine direction by a first repeat pitch distance substantially equal to the first pitch length;
   converting a first portion of the substrate into one of a backsheet and a topsheet on the individual absorbent articles of the first series;
   activating a second portion of the substrate to provide an activated region, wherein the activated region of the substrate is stretched in the machine direction to define a second repeat pitch distance separating consecutive graphics on the second portion of the substrate, and wherein the second repeat pitch distance is substantially equal to the second pitch length; and
   converting the the second portion of the substrate into one of a backsheet and a topsheet on the individual absorbent articles of the second series.

2. The method of claim 1, wherein the printing plate is disposed on a plate roller, and wherein the step of printing a series of graphics further comprises rotating the plate roller.

3. The method of claim 1, wherein the printing station comprises an endless belt with n printing plates disposed thereon, wherein n is 2 or greater, and wherein the step of printing a series of graphics further comprises advancing the endless belt to move each printing plate into contact with the substrate to print a repeating series of n graphics on the substrate.

4. The method of claim 1, further comprising the step of activating the substrate in a cross direction.

5. The method of claim 3, wherein each of the n graphics are different from each other.

6. The method of claim 1, further comprising the step of activating the substrate in a cross direction.

7. The method of claim 1, further comprising the steps of rotating a first roller about a shaft in a first direction, the first roller comprising teeth; and
   rotating a second roller about a shaft in a second direction adjacent the first roller, the second roller comprising teeth, wherein the teeth of the first roller intermesh with the teeth of the second roller.

8. The method of claim 7, further comprising the step of adjusting a center-to-center distance of the first roller and the second roller.

9. The method of claim 7, further comprising the step of advancing the substrate through a nip formed between the first roller and the second roller.

10. The method of claim 9, further comprising the step of adjusting the nip.

* * * * *